United States Patent [19]
Santora, II et al.

[11] Patent Number: 5,804,570
[45] Date of Patent: Sep. 8, 1998

[54] METHOD OF LESSENING THE RISK OF NON-VERTEBRAL BONE FRACTURES

[75] Inventors: Arthur C. Santora, II, Watchung; David B. Karpf, North Brunswick; William J. Polvino, Bridgewater; Deborah Ruth Shapiro, Edison; Desmond E. Thompson, Martinsville; Ashley John Yates, Westfield, all of N.J.

[73] Assignee: Merck & Co., Inc., Rahway, N.J.

[21] Appl. No.: 867,987

[22] Filed: Jun. 3, 1997

Related U.S. Application Data

[63] Continuation of Ser. No. 419,631, Apr. 10, 1995, abandoned, which is a continuation-in-part of Ser. No. 390,462, Feb. 17, 1995, abandoned.

[51] Int. Cl.$^6$ .................................................. A61K 31/66
[52] U.S. Cl. ........................................ 514/108; 514/102
[58] Field of Search ...................... 514/102, 108

[56] References Cited

U.S. PATENT DOCUMENTS

| | | |
|---|---|---|
| 3,683,080 | 8/1972 | Francis et al. . |
| 4,621,077 | 11/1986 | Rosini et al. . |
| 4,922,007 | 5/1990 | Kieczykowski et al. ................. 562/13 |
| 5,270,365 | 12/1993 | Gertz et al. ............................ 514/108 |
| 5,366,965 | 11/1994 | Strein . |
| 5,403,829 | 4/1995 | Lehtinen et al. ........................ 514/102 |
| 5,431,920 | 7/1995 | Bechard ................................. 424/480 |
| 5,462,932 | 10/1995 | Brenner et al. ......................... 514/108 |
| 5,616,571 | 4/1997 | Daifotis et al. . |

OTHER PUBLICATIONS

Riggs, M.D., et al., "The Prevention and Treatment of Osteoporsis", The New England Journal of Medicine, 327(9), Published Aug. 27, 1992, pp. 620–627.

McClung, M.R. et al., "Alendronate Prevents or Reverse Bone Loss at the Spine & Hip in Recently Menopausal Women", J. of Bone Mineral Research, 8(Suppl. 1):S141 (1993) (Abstract Only).

Wardlaw, Ph.D., RD, "Putting Osteoporosis in Perspective", Journal of the American Dietitic Association, 93(9), Sep. 1993, pp. 1000–1006.

Balena et al., "The Effects of 2–Year Treatment With the Aminobisphosphonate Alendronate on Bone Metaboliam, Bone Histomorphometry, and Bone Strength in Ovariectomized Nonhuman Primates", The Journal of Clinical Investigation, 92(6), Published Dec. 1993, pp. 2577–2586.

Kanis et al., Osteoporosis, Blackwell Science Ltd., Oxford, U.K., pp. 170 and 173 (1994).

Riggs et al., N. Eng. J. Med., vol. 327 (1992), No. 9, pp. 620–627, "The prevention and treatment of osteopororisis".

Wardlaw, J. of Amer. Diet Assoc. 93(9), 1993, pp. 1000–1006, "Putting osteoporosis in perspective".

Balena et al., J. of Clin. Invest. 92(6), 1993, pp. 2577–2586, "The effects of 2–year treatment with the aminobisphosphonate alendronate one bone metabolism, bone histomorphometry . . . ".

McClung, M.R. et al 1993 "Alendronate Prevents or Reverses Bone Loss at the Spine and Hip in Recently Menopausal Women" J. Bon Min. Res. 8 (Supp. 11):S141 (Abstract).

Mundy, G.R. 1994 "New Drugs for Bone Diseases" Drugs of Today 30(7):589–597.

Cauley, J.A. et al 1995 "Estrogen Replacement Therapy and Fractures in Older Women" Ann. Int. Med 122 (1): 9–16.

(List continued on next page.)

Primary Examiner—S. Mark Clardy
Assistant Examiner—Robert H. Harrison
Attorney, Agent, or Firm—Anthony D. Sabatelli; Joanne M. Giesser

[57] ABSTRACT

Alendronate, a bisphosphonate, when administered daily over a substantial period of time, can reduce the rate of non-vertebral fractures, in post-menopausal women.

16 Claims, 1 Drawing Sheet

OTHER PUBLICATIONS

Axelrod, D.W. et al, 1994 "Results of Long–Term Cyclical Etidronate Therapy . . . " J. Bone Min Res 9 (Supplement 1): S 136.

Fleisch, 1989 "Bisphosphonates: A New Class of Drugs in Diseases of Bone and Calcium Metabolism" Rec. Results in Cancer Res. 116: 1–28.

Rodan, G. and Balena 1993 "Bisphosphonates in the Treatment of Metabolic Bone Diseases" Ann. Med. 25: 373–378.

Fleisch 1991 "Bisphosphonates" Drugs 42(6): 919–944.

Riggs et al. 1990 "Effect of Fluoride Treatment on Fracture Rate . . . " New Eng. J. Med 322: 802–809.

Lufkin 1994 "Palmidronate: An Unrecognized Problem in Gastrointestinal Tolerability" Osteoporosis Intl 4: 320–322.

Harris, S.T. et al 1993 "Four Year Study of Intermittent Cyclic Etidronate Treatment . . . " Am J. Med. 95: 557–567.

Black, D. M. et al 1993 "Design of the Fracture Intervention Trial" Osteoporosis Intl. Suppl. 3: 529–539.

Burger, H. et al. 1994 "Vertebral Deformities as Predictors of Non–Vertebral Fractures" Brit. Med. J. 309: 991–992.

Anon "FDA Committee on Miacalcin Spray Benefits" and Etidronate Rejected by Advisory Committee Scrip No. 1979, Nov. 29, 1994 pp. 26–27.

Watts, N.B. et al 1990 "Intermittent Cyclical Etidronate Treatment of Postmenopausal Osteoporsis" New Eng J. Med 323 (2) 73–79.

Kanis, J.A. et al 1987 "Effects of Intravenous Etidronate Disodium on Skeletal and Calcium Metabolism" Am J Med. 82 (Suppl 2A): 55–70.

Storm, T. et al 1990 "Effect of Intermittent Cyclical Etidronate Therapy . . . " New Eng J Med 322(18): 1265–1271.

Heaney, R. P. et al "Etidronate Disodium in Postmenopausal Osteoporosis" Clin. Pharm. Therap. 20(5): 593–604 1976.

Gibbs, C.J. et al. 1986 "Osteomalacia in Paget's Disease . . . " Brit. Med. J. 292: 1227–1229.

Sivera, P. et al 1994 "Clinical and Haematological Improvement . . . " Br. J. Haematol. 86: 397–398.

Heany, R.P. et al 1994 "Fluoride and Osteoporsis" Ann. Int. Med. 120(8): 689–690.

Nachtigall, L. E. et al. 1979 "Estrogen Replacement Therapy I . . . " Obstet and Gynec. 53(3): 277–281.

Munk–Jensen, N. et al. 1988 "Reversal of Postmenopausal Vertebral Bone Loss by Oestrogen . . . " Br. Med. J. 296: 1150–1152.

Nordin, B. 1993 "Bone Mass, Bone Loss, Bone Density and Fractures" (Suppl.): S1–7.

METHOD OF LESSENING THE RISK OF NON-VERTEBRAL BONE FRACTURES

This is a continuation of application Ser. No. 08/419,631 filed on Apr. 10, 1995, now abandoned, which is a continuation-in-part of U.S. Ser. No. 08/390,462, filed Feb. 17, 1995, now abandoned, which is hereby incorporated by reference. This invention is related to a method of lessening the risk of non-vertebral bone fractures in post-menopausal women by administering an effective amount of alendronate, a bisphosphonate.

SUMMARY OF THE INVENTION

BACKGROUND OF THE INVENTION

Osteoporosis is a metabolic disease characterized by an age-related decrease in bone mass and strength. The condition primarily affects post-menopausal women, although it may affect elderly men as well. The most common clinical manifestations of osteoporosis are fractures of the vertebrae, hip, and wrist.

Osteoporosis-related fractures are very common, occurring in some 27% of women over the age of 65 and some 60% of those over 80 years of age. Hip fractures are particularly common among women with osteoporosis, occurring in as many as 20% of post-menopausal women. Hip fractures can have very serious consequences—mortality rates of up to 20% in the six months following hospitalization have been observed.

A number of therapies are currently used for the prevention and treatment of osteoporosis, including hormone replacement (estrogen), calcitonin, etidronate (a bisphosphonate), ipriflavone, fluoride, Vitamin D, and calcium. The extent of treatment varies worldwide.

While it has been reported that some of the aforementioned treatment agents can increase bone mineral density (BMD), there is no established correlation between increased BMD and a decrease in non-vertebral fractures. While low BMD is correlated with an increased rate of fracture, a higher BMD is not necessarily correlated with an decrease in fracture, particularly with non-vertebral fractures. For example, fluoride has been shown to increase BMD, but the rate of hip fracture also increases.

DESCRIPTION OF THE INVENTION

It has been found in accordance with this invention that the administration of alendronate (4-amino-1-hydroxybutylidene-1,1-bisphosphonate) is useful in lessening the risk of non-vertebral fractures in osteoporotic post-menopausal women. Furthermore, this risk reduction is maintained and the risk is even lowered with the long-term administration of alendronate. Thus, this invention provides a method of reducing the risk of non-vertebral fractures by administering an effective amount of alendronate or a pharmaceutically acceptable salt to osteoporotic women. Another object of this invention is to reduce the risk of hip and/or wrist fractures by administering an effective amount of alendronate or pharmaceutically acceptable salt thereof for a substantial period of time.

It has been surprisingly found that the incidence of non-vertebral fracture rates can be reduced when an effective amount of alendronate is administered over a substantial period of time. The decrease in the risk of non-vertebral fractures is estimated to be at least about 20%, preferably at least about 25%, and even more preferably at least about 29% compared to placebo. Particularly surprising is that the absolute risk for non-vertebral fractures (compared to placebo) is less after three years administration than after one or two years administration.

It has also been found in accordance with this invention that the increase in bone mineral density observed with the administration of alendronate is positively associated with a decrease in non-vertebral fractures. This indicates that when administered for a substantial period of time, alendronate not only decreases the rate which bone is resorbed, but also acts positively to produce a strengthened bone.

The woman who receives alendronate according to this invention is suffering from osteoporosis, i.e., has a bone mineral density (BMD) which is at least about two or two and one-half standard deviations below the norm of women of premenopausal women.

Figure 1:
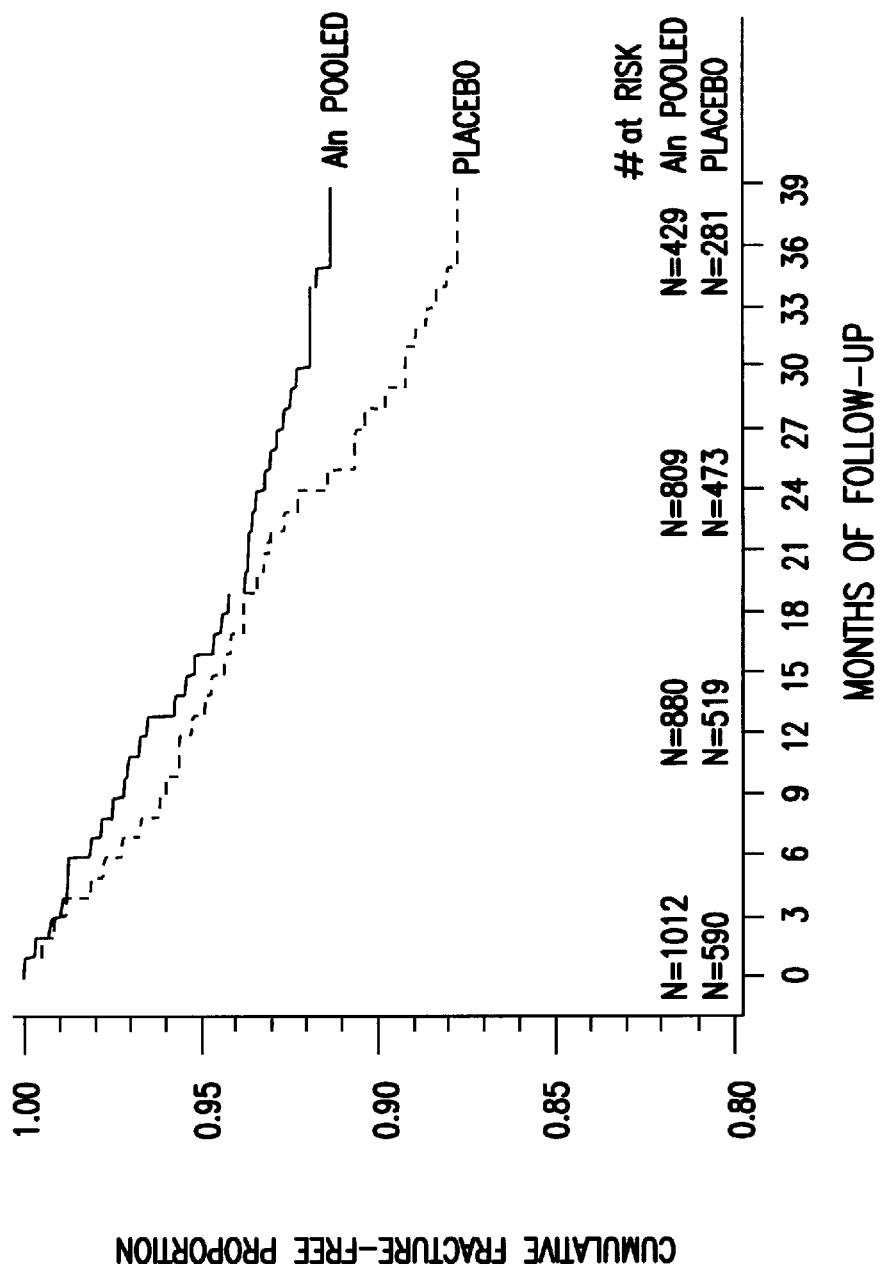
FIG. 1 is a plot showing the cumulative survival function of time to first occurrence of non-vertebral fractures, calculated using the lifetable method, as described in Example 2. Data is the pooled result of five separate clinical studies. At the end of three years, treatment-related differences are statistically significant.

Throughout the specification and claims the following definitions shall apply:

"Effective amount" shall mean at least the amount of alendronate required to decrease the risk of fracture rate, but less than a toxic amount.

"Substantial period of time" means an amount of time which is long enough to allow the bones of the patient to have an increased bone mineral density (BMD) and strength such that they are more resistant to fractures. A typical substantial period of time is a long period of time, and is in excess of two years, and is preferably at least about three years.

"Substantially daily" means that the administration is intended to be daily, but the patient may occasionally inadvertently skip doses, such that the overall effect is not different from that observed when a patient receives the dosage daily.

"Elderly" means that age is equal to or greater than 65 years.

"Non-elderly" means that age is less than 65 years.

"PYR" means person-years-at-risk, and is calculated by summing each patient's time in the study through their first event (non-vertebral fracture) or the end of the trial, whichever occurs first.

Alendronate may be prepared according to any of the processes described in U.S. Pat. Nos. 5,019,651, 4,992,007, and U.S. application Ser. No. 08/286,151, filed Aug. 4, 1994, each of which is hereby incorporated by reference. The pharmaceutically acceptable salts of alendronate include salts of alkali metals (e.g., Na, K), alkali earth metals (e.g., Ca), salts of inorganic acids, such as HCl and salts of organic acids such as citric acid and amino acids. Sodium salt forms are preferred, particularly the monosodium salt trihydrate form.

The compounds of the present invention can be administered in oral dosage forms such as tablets, capsules (each of which includes sustained release or timed release formulations), pills, powders, granules, elixirs, paste, tinctures, suspensions, syrups, dissolvable forms, and emulsions. Likewise they may be administered in an intravenous (bolus or infusion), intraperitoneal, subcutaneous, or intramuscular form, all using forms well known to those of ordinary skill in the pharmaceutical arts. An effective but non-toxic amount of the compound desired can be used as a fracture-preventing agent.

Patients preferably will receive alendronate substantially daily for a substantial period of time in order for the effect to be observable. This means that the patient will receive alendronate at least one-half of the days in a treatment period, with the treatment period lasting at least one year, and is preferably longer, up to and exceeding three or more years. In a preferred embodiment, the patient will receive alendronate substantially daily for at least three years in order to experience the greatest benefit. It is envisioned that a patient receiving such a long-term therapy may experience occasional periods when alendronate is not administered; but since alendronate has a long active life in the bone, this is considered within the scope of the invention provided that the patient receives alendronate at least one-half of the days in the preceding six month period. Also, it is within the scope of this invention that the alendronate be administered on a cyclical regime, i.e., the patient may receive alendronate for a given period of time, i.e., one month, then may be taken off the alendronate (and may or may not be given additional bone-promoting or bone absorption-inhibiting agents, and/or hormonal therapy) for a second period of time, and returned to alendronate therapy.

The dosage regime utilizing the claimed method is selected in accordance with a variety of factors including type, age, weight, sex, and medical condition of the patient; the severity of the condition to be treated; the route of administration; the renal and hepatic function of the patient; and the particular compound or salt thereof employed. An ordinarily skilled physician or clinician can readily determine and prescribe the effective amount of the drug required to prevent bone fractures.

Oral dosages of the present invention, when used to prevent bone fractures will range from between 0.05 mg per kg of body weight per day (mg/kg/day) to about 1.0 mg/kg/day. Preferred oral dosages in humans may range from daily total dosages of about 2.5–50 mg/day over the effective treatment period, and a preferred amount is 2.5, 5, 10 or 20 mg/day. The dosages may be varied over a period of time, such that a patient may receive a high dose, such as 20 mg/day for a treatment period, such as two years, followed by a lower dose thereafter, such as 5 mg/day thereafter. Alternatively, a low dose (i.e., approximately 5 mg) may also be administered for a longer term with similar beneficial effects.

Alendronate may be administered in a single daily dose or in a divided dose. It is desirable for the dosage to be given in the absence of food, preferably from about 30 minutes to 2 hours prior to a meal, such as breakfast to permit adequate absorption.

In the methods of the present invention, the active ingredient is typically administered in admixture with suitable pharmaceutical diluents, excipients or carriers (collectively referred to herein as "carrier materials") suitably selected with respect to the intended form of administration, i.e., oral tablets, capsules, elixirs, syrups and the like and consistent with conventional pharmaceutical practices. For example, for oral administration in the form of a tablet or capsule, the active ingredient can be combined with an oral, non-toxic, pharmaceutically acceptable inert carrier such as lactose, starch, sucrose, glucose, methyl cellulose, magnesium stearate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture of active ingredient (s) and inert carrier materials. Suitable binders may include starch, gelatin, natural sugars such as glucose, anhydrous lactose, free-flow lactose, beta-lactose, and corn sweeteners, natural and synthetic gums, such as acacia, tragacanth or sodium alginate, carboxymethyl cellulose, polyethylene glycol, waxes, cros carmallose sodium, and the like. Lubricants used in these dosage forms include sodium oleate, sodium stearate, magnesium stearate, sodium benzoate, sodium acetate, sodium chloride and the like. A particularly preferred tablet formulation is that described in U.S. Pat. No. 5,358,941, which is hereby incorporated by reference.

The compounds used in the instant method may also be coupled with soluble polymers as targetable drug carriers. Such polymers can include polyvinylpyrrolidone, pyran co-polymer, polyhydroxylpropyl-methacrylamide and the like.

The combined analysis of five clinical trial shows that alendronate, when administered over a substantial period of time can reduce the risk of a non-vertebral fracture. For example, in patients receiving alendronate, the estimated cumulative incidence of fracture after three years was 9.0% and the overall incidence rate for non-vertebral fractures was 3.26 per 100 Person Years at Risk (PYR). In contrast, for patients receiving placebo, the estimated cumulative incidence was 12.6% after three years and the overall rate of non-vertebral fractures per 100 PYR was 4.45. The lifetable (proportional hazards model) estimate of the overall risk reduction for non-vertebral fractures was 29% with a 95% confidence interval of (0.3%, 49.8%). The p-value associated with the observed reduction in risk was p=0.048. The analysis of rates gave an identical p-value and similar confidence interval.

Also, the effect of reducing the risk of non-vertebral fracture is the same for elderly (at least 65 years of age) and non-elderly (age less than 65 years) patients. Thus another aspect of this invention is a method of decreasing the risk of non-vertebral fracture in elderly osteoporotic women by administering an effective amount of alendronate for a substantial period of time.

Further, it has been shown that the decrease in absolute risk of non-vertebral fractures due to alendronate treatment increases with time.

The following non-limiting examples are presented to better illustrate the invention.

EXAMPLE 1

Postmenopausal women having a "low" lumbar spinal bone mineral density, defined as either a bone mineral density (BMD) of less than or equal to 0.92 g/cm$^2$ (+or–0.02 g/cm$^2$) as measured by Lunar DPX method, or less than or equal to 0.80 g/cm$^2$ (+or–0.02 g/cm$^2$) as measured by the Hologic QDR method are considered to have osteoporosis. This definition corresponds to a BMD of approximately two and one-half standard deviations below the mean BMD of mature pre-menopausal Caucasian women in the United States. Patients are otherwise in good health based on medical history, a physical examination and a laboratory screening evaluation.

Data was collected on 1602 patients from five study groups (cohorts). 1012 patients were treated with alendronate, from one of the following oral dosage regimes: A) 5 mg daily for two or three years; B) 10 mg daily for two or three years; C) 20 mg for two years, followed by 5 mg for one year; D) 2.5 mg daily for two years; E) 40 mg daily for three months, followed by 2.5 mg daily for 21 months; or F) 20 mg daily for two years. 590 patients received placebo. Additionally, all patients received dietary evaluation and instruction on calcium intake. Almost all received calcium supplements to provide 500 mg elemental calcium (as carbonate) to ensure nutritional adequacy.

TABLE 1 presents the number of patients, the number of non-vertebral fractures and the person-years-at-risk (PYR) by treatment group for each of the cohorts. The total number of non-vertebral fractures reported was 133: there were 60 in the placebo group and 73 in the alendronate group. The total number of PYR accumulated was 3587:1347 in the placebo group and 2240 in the alendronate groups.

TABLE 1

Combined Studies
Non-Vertebral Fractures and
Person-Years-At-Risk (PYR)

| COHORT | PLACEBO | | | ALBND[1] | | |
|---|---|---|---|---|---|---|
| | N | Cases | PYR | N | Cases | PYR |
| #1 | 31 | 3 | 49 | 93 | 8 | 161 |
| #2 | 192 | 21 | 486 | 286 | 28 | 720 |
| #3 | 205 | 17 | 529 | 311 | 17 | 805 |
| #4 | 71 | 3 | 128 | 140 | 2 | 256 |
| #5 | 91 | 16 | 154 | 182 | 18 | 298 |
| All Combined | 590 | 60 | 1347 | 1012 | 73 | 2240 |

[1]ALEND is alendronate-treated

TABLE 2, below, reports the rate of non-vertebral fractures per 100 PYRs by treatment group for each of the five cohorts. In the placebo group, the rates ranged from 2.34 to 10.38 non-vertebral fractures per 100 PYR. The rates in the alendronate group ranged from 0.78 to 6.04. The last column of TABLE 2 reports these rates as ratios versus placebo by cohort. The ratios ranged from 0.33 to 0.90 and confirm that for each of the cohorts, the rates in the alendronate groups were consistently lower than those in the placebo group.

TABLE 2

Combined Studies
Non-Vertebral Fractures per 100 PYR

| COHORT | PLACEBO | ALENDRONATE | Ratio of Rates ALN/PLC |
|---|---|---|---|
| #1 | 6.07 | 4.97 | 0.82 |
| #2 | 4.32 | 3.89 | 0.90 |
| #3 | 3.21 | 2.11 | 0.66 |
| #4 | 2.34 | 0.78 | 0.33 |
| #5 | 10.38 | 6.04 | 0.58 |
| All Combined | 4.45 | 3.26 | 0.73 |

The data were analyzed to determine if there was a difference between the response between the elderly (age 65 or older) or non-elderly (age less than 65) women. A Cox proportional hazards model that included age as well as treatment as model effects and protocol as a stratification factor was also examined. Age was not a significant factor whether evaluated as a continuous variable or as a categorical value in either models. The relative risk estimated in both models was virtually identical to 1. This means that there is no difference in effect in elderly versus non-elderly patients. Results are presented below in TABLES 3 and 4.

TABLE 3

Non-Vertebral Fractures in Elderly

| | Placebo | Alendronate | Risk Reduction |
|---|---|---|---|
| N | 284 | 479 | |
| Cases | 34 | 37 | |
| PYR | 636 | 1036 | |
| Cumulative Incidence | 14.6% | 9.4% | 36% |
| Rate of fracture per 100 PYR | 5.35 | 3.57 | 33% |

TABLE 4

Non-Vertebral Fractures in Non-Elderly

| | Placebo | Alendronate | Risk Reduction |
|---|---|---|---|
| N | 306 | 533 | |
| Cases | 26 | 36 | |
| PYR | 711 | 1204 | |
| Cumulative Incidence | 10.8% | 8.5% | 21% |
| Rate of fracture per 100 PYR | 3.66 | 2.99 | 18% |

The data was also analyzed for the effect of the years of treatment. Results are presented in TABLE 5, below.

TABLE 5

Yearly Incidence of Non-Vertebral Fractures

| Study Year | Placebo | Alendronate | Ratio of Rates ALN/PLB |
|---|---|---|---|
| 1 | 4.88 | 3.53 | 0.72 |
| 2 | 4.09 | 3.60 | 0.88 |
| 3 | 4.27 | 2.12 | 0.50 |

EXAMPLE 2

Lifetable Calculations

Cumulative clinical fracture-free proportions and interval estimates were calculated using the lifetable method for the pooled-over-protocol populations; this pooling was done for ease of presentation. Between treatment comparisons were based on the log rank statistic from a lifetable model with protocol as a stratification factor. Relative risk was calculated using a Cox proportional hazards model for grouped data with treatment as the model effect and protocol as a stratification factor. FIG. 1 is the plot of the cumulative clinical fracture-free proportion. Treatment related differences in cumulative proportions increase in the third year.

Tables 6 and 7, below show summary statistics for the lifetable model for the alendronate and placebo groups, respectively. At the end of three years of follow-up, the estimated cumulative proportion of patients with clinical fracture was 0.090 in the alendronate group and 0.126 in the placebo group. The risk reduction from non-vertebral fracture was estimated to be 29.3% with a 95% confidence interval of [0.3%, 49.8%]. The p-value associated with this difference is p=0.047.

TABLE 6

Lifetable Survival Estimates
Pooled Alendronate Treatment Groups

| Interval (Months) | No. non-Vertebral Fractures | Number censored | Effective Sample Size | Cumulative Probability of Failure | Cumulative Probability of Survival | Survival Standard Error |
|---|---|---|---|---|---|---|
| 0–3 | 10 | 39 | 992.5 | 0 | 1.0000 | 0 |
| 3–6 | 8 | 22 | 952.0 | 0.0101 | 0.9899 | 0.00317 |
| 6–9 | 9 | 20 | 923.0 | 0.0184 | 0.9816 | 0.00430 |
| 9–12 | 6 | 18 | 895.0 | 0.0280 | 0.9720 | 0.00531 |
| 12–15 | 12 | 15 | 872.5 | 0.0345 | 0.9655 | 0.00590 |
| 15–18 | 9 | 8 | 849.0 | 0.0478 | 0.9522 | 0.00696 |
| 18–21 | 5 | 10 | 831.0 | 0.0579 | 0.9421 | 0.00765 |
| 21–24 | 4 | 147 | 747.5 | 0.0635 | 0.9365 | 0.00802 |
| 24–27 | 3 | 184 | 578.0 | 0.0685 | 0.9315 | 0.00835 |
| 27–30 | 4 | 10 | 478.0 | 0.0734 | 0.9266 | 0.00877 |
| 30–33 | 0 | 5 | 466.5 | 0.0811 | 0.9189 | 0.00951 |
| 33–36 | 3 | 283 | 322.5 | 0.0811 | 0.9189 | 0.00951 |
| 36–39 | 0 | 178 | 89.0 | 0.0897 | 0.9103 | 0.01060 |

TABLE 7

Lifetable Survival Estimates
Placebo Treatment Groups

| Interval (Months) | No. Non-Vertebral Fractures | Number censored | Effective Sample Size | Cumulative Probability of Failure | Cumulative Probability of Survival | Survival Standard Error |
|---|---|---|---|---|---|---|
| 0–3 | 7 | 7 | 586.5 | 0 | 1.0000 | 0 |
| 3–6 | 9 | 12 | 570.0 | 0.0119 | 0.9881 | 0.00448 |
| 6–9 | 7 | 14 | 548.0 | 0.0275 | 0.9725 | 0.00679 |
| 9–12 | 4 | 11 | 528.5 | 0.0400 | 0.9600 | 0.00817 |
| 12–15 | 5 | 13 | 512.5 | 0.0472 | 0.9528 | 0.00888 |
| 15–18 | 3 | 5 | 498.5 | 0.0565 | 0.9435 | 0.00971 |
| 18–21 | 4 | 9 | 488.5 | 0.0622 | 0.9378 | 0.01020 |
| 21–24 | 8 | 86 | 437.0 | 0.0699 | 0.9301 | 0.01080 |
| 24–27 | 4 | 69 | 351.5 | 0.0869 | 0.9131 | 0.01220 |
| 27–30 | 4 | 4 | 311.0 | 0.0973 | 0.9027 | 0.01310 |
| 30–33 | 3 | 0 | 305.0 | 0.1089 | 0.8911 | 0.01420 |
| 33–36 | 2 | 198 | 203.0 | 0.1177 | 0.8823 | 0.01490 |
| 36–39 | 0 | 102 | 51.0 | 0.1264 | 0.8736 | 0.01600 |

What is claimed is:

1. A method of reducing the risk of non-vertebral fractures in an osteoporotic female comprising administering an effective amount of alendronate or a pharmaceutically acceptable salt thereof.

2. The method according to claim 1 wherein the alendronate is administered orally.

3. The method according to claim 2 wherein the dose is from 2.5 mg to 20 mg daily.

4. The method according to claim 3 wherein the dose is 10 mg daily.

5. The method according to claim 2 wherein the alendronate is administered substantially daily for a period of more than two years.

6. The method according to claim 2 wherein the alendronate is administered substantially daily for a period of at least about three years.

7. The method according to claim 1 wherein the female is elderly.

8. A method of reducing the risk of non-vertebral bone fractures in an osteoporotic postmenopausal female comprising administering to the female from 2.5–20 mg of alendronate or a pharmaceutically acceptable salt thereof substantially daily for a substantial period of time.

9. A method according to claim 8 wherein the female is elderly.

10. The method according to claim 1 wherein the alendronate is administered for a substantial period of time.

11. The method according to claim 3 wherein the dose is 2.5 mg daily.

12. The method according to claim 3 wherein the dose is 5 mg daily.

13. The method according to claim 8 wherein the dose is 2.5 mg daily.

14. The method according to claim 8 wherein the dose is 5 mg daily.

15. The method according to claim 8 wherein the dose is 10 mg daily.

16. The method according to claim 8 wherein the dose is 20 mg daily.

* * * * *